United States Patent [19]

Pattison

[11] 4,004,073
[45] Jan. 18, 1977

[54] POLYMERIC FLUOROMETHYLATED DIENES

[75] Inventor: Victor A. Pattison, Tonawanda, N.Y.

[73] Assignee: Hooker Chemicals & Plastics Corporation, Niagara Falls, N.Y.

[22] Filed: Feb. 9, 1976

[21] Appl. No.: 656,219

Related U.S. Application Data

[63] Continuation of Ser. No. 411,869, Nov. 1, 1973, abandoned, and a continuation-in-part of Ser. No. 788,009, Dec. 30, 1968, abandoned.

[52] U.S. Cl. .................... 526/252; 526/247; 526/249; 526/253; 526/254; 526/255
[51] Int. Cl.² ............. C08F 136/16; C08F 136/18
[58] Field of Search .............. 526/252, 249, 255

[56] References Cited

UNITED STATES PATENTS

| | | |
|---|---|---|
| 3,035,034 | 5/1962 | McKrisick et al. ............. 260/92.1 R |
| 3,148,175 | 9/1964 | Barr ......................... 260/92.1 R X |
| 3,607,850 | 9/1971 | Smith ........................ 260/92.1 R X |

OTHER PUBLICATIONS

Plakhova et al., Chem. Abstracts, (1962), vol. 57, col. 13596e.
Polymerization Studies Leading to High Strength Chem. Resist Elastomers by Relyea et al., (Cont. No. DA 19-129-AMC-487(N) for U.S. Army Natick Labs by Uniroyal, -6,-1967.

*Primary Examiner*—William F. Hamrock
*Attorney, Agent, or Firm*—Peter F. Casella

[57] ABSTRACT

Polymers and copolymers of

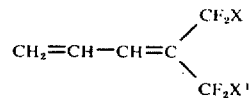

are disclosed, wherein X and X¹ are halogen.

5 Claims, No Drawings

POLYMERIC FLUOROMETHYLATED DIENES

This is a continuation of application Ser. No. 411,869, filed Nov. 1, 1973, now abandoned and a continuation-in-part of Ser. No. 788,009, filed Dec. 30, 1968, now abandoned.

This invention relates to novel fluoromethylated compounds and processes for producing such compounds. More particularly, this invention relates to polymers and copolymers of fluoromethylated butadiene.

The polymers of the present invention are those obtained by polymerizing monomers of the general formula

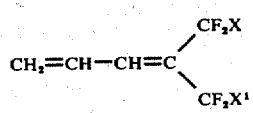

wherein X and $X^1$ are halogen, either alone in a homopolymerization reaction, or in the presence of at least one other dissimilar monomer copolymerizable therewith.

The fluoromethylated diene monomer may be readily prepared by reacting a fluoroacetone of the formula

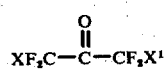

wherein X and $X^1$ are as previously defined, with propylene, in the presence of a Friedel-Crafts catalyst, to yield an intermediate fluoromethylated alkenol of the formula

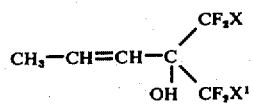

wherein X and $X^1$ are as previously defined. The resulting alkenol is then dehydrated to yield the monomeric butadiene. Depending upon whether or not it is desired to isolate the intermediary alkenols, the two steps of the reaction may be carried out separately or together; that is, the dehydration agent may optionally be added to the olefin-fluoroacetone adduct without purification of the alkenols.

The fluoroacetone-olefin adduct is prepared by combining fluoroacetone and the appropriate olefin in a molar ratio of up to a 100 mole excess of either reactant, although a ratio of from 1:1 to 1:2 is preferred. Optionally, a solvent may be utilized; convenient solvents for the reaction include hexane or pentane, or other appropriate solvents inert to the conditions of the reaction. The reaction is carried out in the presence of a conventional Friedel-Crafts catalyst and at a temperature within the range of from about −100° to about 50° C, preferably from about −50° to 0° C.

Aluminum trichloride is an effective catalyst. Other suitable Friedel-Crafts type catalysts include boron trifluoride, tin chloride, zinc chloride, antimony fluoride and other aluminum halides.

The intermediate fluoromethylated alkenols are conveniently isolated from the reaction mixture by fractional distillation.

The reaction of fluoroacetones with the propylene evidently occurs with an alkyl rearrangement to form, as previously stated

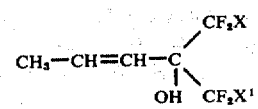

The adductive step provides a product comprised primarily of the stable trans isomer of the 2-alkenol, with the relatively unstable cis isomer present only in trace amounts. The isomers may be separated, if desired, by suitable gas chromatography procedures.

If isolation of the intermediate fluoromethylated alkenol is not desired, the dehydration agent may be added directly to the reaction mixture containing the fluoroacetone-olefin adduct.

To obtain the dehydration product, the dehydration agent is added after the adductive step of the reaction is complete and the reaction mixture has been heated to from about 20° to 300° C, preferably from about 50° to 150° C. Suitable dehydration agents include phosphorus pentoxide and concentrated sulfuric acid. While the dehydration agent may be added in proportions ranging from about 0.2 to 1000 moles per mole of fluoromethylated alkenol, the reaction is most efficiently carried out with an excess of the dehydration agent of from about 10 to about 30 moles per mole of alkenol present.

The polymerizable dehydration product is predominantly 1, 1-bis (halodifluoromethyl)-1,3- butadiene, although minor amounts of 1,1-bis (halodifluoromethyl) — tetrahydrofuran may be present. The conditions are controlled so that polymerization of the product is not induced prematurely.

The fluoromethylated butadiene may be polymerized or copolymerized with one or more monomers copolymerized therewith by conventional methods. The polymers and copolymers are useful as coating compositions, and are particularly valuable for their ability to confer water and oil repellancy to fibrous materials coated therewith.

The homopolymers of the fluoromethylated butadiene are characterized by the repeating units

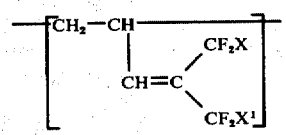

in the skeletal chain, wherein X and $X^1$ are as previously defined.

Homopolymerization of the fluoromethylated butadienes may be effected by polymerization methods known in the art, for example, by emulsion, solution, bulk or suspension techniques, with free radical generators such as benzoyl peroxide, alkali metal persulfates or the like are preferably used to initiate the polymerization reaction.

The monomers may be copolymerized with vinyl monomers such as styrene, acrylamide acrylonitrile, ethyl acrylate, sioprene, haloprene, methylstyrene, vinyl pyrrolidone, vinyl halides, methyl methacrylate and methacryl halides. Particularly efficacious as oil and water-proofing agents are styrene-fluoromethylated butadiene copolymers and the acrylamide-fluoromethylated butadiene copolymers.

The examples which follow are provided to more clearly illustrate the nature of the present invention. All parts and percentages are by weight, and all temperatures are in degrees centigrade, unless otherwise specified.

EXAMPLE 1

PREPARATION OF PROPYLENE - HEXAFLUORO ACETONE ADDUCTS

A mixture of 166 parts of fluoroacetone, 84 parts of propylene and 2 parts aluminum chloride in 1630 parts of pentane was allowed to warm slowly from $-30°$. At about $-15°$ there was a gentle exotherm after which the reaction was stirred for 1 hour at ambient temperatures, then washed with 5 percent hydrochloric acid, dried over sodium sulfate and distilled (18 inch Vigreaux) to yield 150 parts (72 percent) of product boiling at $97°-100°$. The composition of this product is 60 percent trans -1,1-bis (trifluoromethyl)-2-buten-1-ol, 3 percent cis -1,1-bis (trifluoromethyl) -2-buten-1-ol and 37 percent 1,1-bis (trifluoromethyl)-3-buten-1-ol. Elemental analyses, infrared and nuclear magnetic resonance spectra confirmed the identity of the products.

EXAMPLE 2

PREPARATION OF PROPYLENE - CHLORO - PENTAFLUOROACETONE ADDUCTS

The process of Example 1 was repeated using 182 parts of chloropentafluoroacetone and 84 parts propylene yielding 82 percent (184 parts) of product boiling at $120°-130°$. A mixture of isomers corresponding to that obtained in Example 1 was obtained. Elemental analyses, infrared and nuclear magnetic resonance spectra confirmed the identity of the product.

EXAMPLE 3

PREPARATION OF FLUOROMETHYLATED DIENE

A mixture of alkenols (272 parts) prepared in Example 1 from propylene and hexafluoroacetone and 740 parts of concentrated sulfuric acid were placed in a distillation flask fitted with a magnetic stirrer and an 8 inch Vigreaux column. The temperature of the reaction mixture was slowly raised until clear liquid started to distill at about $100°$. The temperature was held at $100°-110°$ while 150 parts (59 percent) of essentially pure 1, 1-bis (trifluoromethyl)-1,3- butadiene distilled at 75 degrees. This product redistilled at $70°-72°$. Elemental analyses, infrared and nuclear magnetic resonance spectra confirmed the identity of the product.

EXAMPLE 4

PREPARATION OF 1-CHLORO-1,1-DIFLUORO-2-TRIFLUOROMETHYL -2, 4-PENTADIENE

The process of Example 3 was repeated using 22.4 parts of the propylene-chloropentafluoroacetone adduct prepared in Example 2 which was distilled slowly from 90 grams of concentrated sulfuric acid at 50 mm pressure. The distillate (12 parts) was dissolved in ether, washed with 5 percent sodium hydroxide solution, then washed with water and dried over sodium sulfate. Distillation (8 inch Vigreaux) effected 1-chloro-1,1-difluoro-2-trifluoromethyl-2,4-pentadiene boiling at $101°-102°$. Elemental analyses, infrared and nuclear magnetic resonance spectra confirmed the identity of the product.

EXAMPLE 5

BULK POLYMERIZATION OF 1,1-BIS -(TRIFLUOROMETHYL) -1,3-BUTADIENE

A mixture of 1.90 parts of 1,1-bis-(trifluoromethyl)-1,3-butadiene and 0.010 parts of benzoyl peroxide was placed in a vessel, flushed with nitrogen and heated at $60°$ for 66 hours. The reaction mixture was stripped of monomer by heating at $110°/1$ mm for 1 hour. The polymeric residue obtained in essentially quantitive yield had a molecular weight of 4500. Infrared spectra confirmed the identity of the product.

EXAMPLE 6

EMULSION POLYMERIZATION OF 1,1-BIS-(TRIFLUOROMETHYL)-1,3-BUTADIENE

A mixture of 11.8 parts of 1,1-bis-(trifluoromethyl)-1,3-butadiene, 34 parts of water, 6.060 parts of potassium persulfate and 0.36 parts of sodium lauryl sulfate was placed in a vial, flushed with nitrogen and heated with vigorous stirring at $50°-60°$ for 20 hours. Evaporation of the water from the resultant emulsion gave a clear, tough polymer in essentially quantitative yield, having a molecular weight of 83,000. A clear, water-white, tough film was cast from its acetone solution. The infrared spectrum is similar to that from the bulk polymerization.

EXAMPLE 7

PREPARATION OF COPOLYMER OF 1,1-BIS-(TRIFLUOROMETHYL)-1,3-BUTADIENE AND ACRYLAMIDE

The emulsion polymerization process of Example 6 was repeated using equimolar quantities of 1,1-bis-(trifluoromethyl)-1,3- butadiene and acrylamide. A high molecular weight 1:1 copolymer of 1,1-bis-(trifluoromethyl)-1,3-butadiene and acrylamide was obtained.

EXAMPLE 8

PREPARATION OF A METHYLOLATED COPOLYMER OF 1,1-BIS-(TRIFLUOROMETHYL)-1,3-BUTADIENE AND ACRYLAMIDE

A mixture of 3.6 parts of acrylamide, 9.8 parts of 1,1-bis(trifluoromethyl)-1,3-butadiene, 24 parts of water, 0.06 parts of potassium persulfate, and 0.36 parts of sodium lauryl sulfate were heated and stirred at $50°-60°$ for 20 hours to form a viscous emulsion. This emulsion was diluted with 50 parts of water and brought to pH 8.0 with sodium carbonate. At this point 8.5 parts of 37 percent formaldehyde was added, and the emulsion was stirred overnight at ambient temperatures to produce a resin which is a methylolated 1:1 copolymer of 1,1-bis(trifluoromethyl)-1,3-butadiene and acrylamide.

EXAMPLE 9

PREPARATION OF COPOLYMER OF 1,1-BIS (TRIFLUOROMETHYL)-1,3-BUTADIENE AND ACRYLONITRILE

The emulsion polymerization process of Example 6 was repeated using equimolar quantities of 1,1-bis(trifluoromethyl)-1,3- butadiene and acrylonitrile. A high molecular weight 1:1 copolymer of 1,1-bis (trifluoromethyl :1, 3- butadiene and acrylonitrile was obtained. A clear, water-white, tough film was cast from its acetone solution. Infrared spectra confirmed the structure of the polymer.

EXAMPLE 10

PREPARATION OF COPOLYMER OF 1,1-BIS (TRIFLUOROMETHYL) -1,3-BUTADIENE AND STYRENE

The emulsion polymerization of Example 6 was repeated using equimolar quantities of 1,1-(trifluoromethyl)-1,3-butadiene and styrene. A high molecular weight (163,000) 1:1 copolymer of 1,1-bis (trifluoromethyl)-1,3-butadiene and styrene was obtained. A clear, water-white, tough film was cast from its acetone solution. Infrared spectra confirmed the structure of the polymer.

EXAMPLE 11

PREPARATION OF COPOLYMER OF 1,1-BIS (TRIFLUOROMETHYL)-1,3-BUTADIENE AND ETHYL ACRYLATE

The emulsion polymerization process of Example 6 was repeated using equimolar quantities of 1,1-bis(trifluoromethyl)-1,3-butadiene and ethyl acrylate. A high molecular weight (110,000) 1:1 copolymer of 1,1-bis(-trifluoromethyl)-1,3-butadiene and ethyl acrylate was obtained. A slightly opaque, nearly water-white film was cast from its acetone solution. Infrared spectra confirmed the structure of the polymer.

EXAMPLE 12

PREPARATION OF COPOLYMER OF 1,1-BIS (TRIFLUOROMETHYL)-1,3-BUTADIENE AND ISOPRENE

The emulsion polymerization process of Example 6 was repeated using equimolar quantities of 1,1-bis(trifluoromethyl)-1,3-butadiene and isoprene. A high molecular weight (173,000) 1:1 copolymer of 1,1-bis(trifluoromethyl)-1,3-butadiene and isoprene was obtained. A slightly opaque, elastomeric film was cast from its acetone solution. Infrared spectra confirmed the structure of the polymer.

It is to be understood that the details provided in the foregoing specification can be modified by those skilled in the art without departing from the scope of the invention.

What is claimed is:

1. Homopolymers of halomethylated dienes of the formula

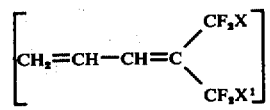

wherein X and X' are halogen and wherein said homopolymers are characterized by the repeating units

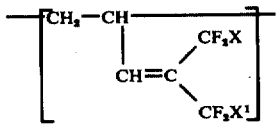

in the skeletal chain produced by the process comprising allowing said halomethylated dienes to polymerize by the use of a free radical catalyst.

2. Homopolymers produced by the process of claim 1 wherein X and X' are fluorine.

3. Homopolymers produced by the process of claim 1 wherein X is chlorine and X' is fluorine.

4. Homopolymers produced by the process of claim 1 wherein said free radical catalyst is an alkali metal persulfate.

5. Homopolymers produced by the process of claim 1 wherein said free radical catalyst is benzoyl peroxide.

* * * * *